US012403896B2

(12) United States Patent
Nezhad

(10) Patent No.: US 12,403,896 B2
(45) Date of Patent: Sep. 2, 2025

(54) MEDICAMENT DISPENSER BASED ON VEHICLE COLLISION

(71) Applicant: Honda Motor Co., Ltd., Tokyo (JP)

(72) Inventor: Benny Nezhad, Dublin, OH (US)

(73) Assignee: Honda Motor Co., Ltd., Tokyo (JP)

( * ) Notice: Subject to any disclaimer, the term of this patent is extended or adjusted under 35 U.S.C. 154(b) by 244 days.

(21) Appl. No.: 18/175,299

(22) Filed: Feb. 27, 2023

(65) Prior Publication Data

US 2024/0286603 A1 Aug. 29, 2024

(51) Int. Cl.
*B60W 30/08* (2012.01)
*A61M 35/00* (2006.01)
*G07C 5/08* (2006.01)
*B60W 60/00* (2020.01)

(52) U.S. Cl.
CPC ............ *B60W 30/08* (2013.01); *A61M 35/00* (2013.01); *G07C 5/08* (2013.01); *A61M 2205/05* (2013.01); *A61M 2205/3303* (2013.01); *B60W 2030/082* (2013.01); *B60W 60/0016* (2020.02); *B60W 2540/221* (2020.02)

(58) Field of Classification Search
CPC ............ B60W 30/08; B60W 60/0016; B60W 2030/082; B60W 2540/221; B60W 2040/0872; A61M 35/00; A61M 2205/05; A61M 2205/3303; A61M 35/20; A61M 2021/0077; G07C 5/08; B60R 2021/0027; B60R 21/00; A61B 5/18; A61B 5/6893; B05B 12/02; B05B 9/01; B05B 9/00; B60K 28/06
See application file for complete search history.

(56) References Cited

U.S. PATENT DOCUMENTS

| | | |
|---|---|---|
| 9,808,463 B1 | 11/2017 | Kawaguchi |
| 10,350,103 B2 | 7/2019 | Martin |
| 10,534,819 B2 | 1/2020 | Ricci |
| 11,075,992 B2 | 7/2021 | Erickson et al. |
| 11,458,995 B2 | 10/2022 | Wolff et al. |

(Continued)

FOREIGN PATENT DOCUMENTS

| | | |
|---|---|---|
| DE | 102020207778 A1 | 12/2021 |
| JP | 6925865 B2 | 8/2021 |

(Continued)

*Primary Examiner* — Scott A Browne
*Assistant Examiner* — Jisun Choi
(74) *Attorney, Agent, or Firm* — Suzanne Gagnon; American Honda Motor Co., Inc.

(57) ABSTRACT

An electronic device and method for control of a medicament dispenser based on a collision of a vehicle is disclosed. The electronic device receives first information from one or more first sensors associated with a vehicle. The first information corresponds to a collision event of the vehicle. The electronic device receives second information from one or more second sensors associated with the vehicle based on the collision event. The second information corresponds to a set of health parameters associated with an occupant of the vehicle. Thereafter, the electronic device controls one or more medicament dispensers integrated into the vehicle based on at least one health parameter of the set of health parameters. Such dispensers are controlled to dispense one or more medicaments on at least one body part of the occupant.

20 Claims, 9 Drawing Sheets

(56) References Cited

U.S. PATENT DOCUMENTS

| | | | |
|---|---|---|---|
| 2004/0133082 A1* | 7/2004 | Abraham-Fuchs | A61B 5/6887 340/576 |
| 2017/0028178 A1* | 2/2017 | Skoda | G16H 40/67 |
| 2019/0359056 A1* | 11/2019 | Wilson | B60N 2/0024 |
| 2021/0407687 A1* | 12/2021 | Pasch | A61B 5/747 |
| 2022/0067410 A1 | 3/2022 | Raz et al. | |

FOREIGN PATENT DOCUMENTS

| | | |
|---|---|---|
| KR | 20200119360 A | 10/2020 |
| WO | 2020083549 A1 | 4/2020 |
| WO | 2022042868 A1 | 3/2022 |

\* cited by examiner

MEDICAMENT DISPENSER BASED ON VEHICLE COLLISION

BACKGROUND

Slow response times and delayed medical treatment for people involved in vehicle accidents are major concerns in the field of emergency response. Despite technological and communication advancements, first responders frequently struggle to quickly locate and reach accident scenes, resulting in delays in providing critical medical care to affected individuals. This may have serious consequences for accident victims' health and well-being and may even result in preventable deaths. Most vehicles are equipped with safety measures such as airbags, seatbelts, antilock brakes (ABS), traction control, brake assist, or collision warning to prevent accidents or fatal injuries that may lead to loss of life. Existing safety measures in a vehicle may be useful in minor intensity impacts or collisions, but in high intensity impacts or collisions, they may not be as effective. In some cases, a high intensity collision of the vehicle with an object such as a boulder, a car, a truck, a pavement, or a tree may cause severe injury to one or more occupants of the vehicle or may even cause hemorrhage. Hemorrhage is a loss of blood from a damaged blood vessel that typically involves bleeding from an injured part of the body over time. Severe or chronic hemorrhaging, if left untreated, can result in organ failure, seizures, coma, external bleeding, or even death.

Limitations and disadvantages of conventional and traditional approaches will become apparent to one of skill in the art, through comparison of described electronic devices with some aspects of the present disclosure, as set forth in the remainder of the present application and with reference to the drawings.

SUMMARY

According to an embodiment of the disclosure, an electronic device for control of a medicament dispenser based on a collision of a vehicle is disclosed. The electronic device may include circuitry that may be configured to receive first information from one or more first sensors associated with a vehicle. The first information may correspond to a collision event of the vehicle. The circuitry may be configured to receive second information from one or more second sensors associated with the vehicle based on the collision event. The second information may correspond to a set of health parameters associated with an occupant of the vehicle. Thereafter, the circuitry may be configured to control one or more medicament dispensers integrated into the vehicle based on at least one health parameter of the set of health parameters. Such dispensers may be controlled to dispense one or more medicaments on at least one body part of the occupant.

According to another embodiment of the disclosure, a method for control of medicament dispenser based on a collision of a vehicle is disclosed. The method may include receiving first information from one or more first sensors associated with a vehicle. The first information may correspond to a collision event of the vehicle. The method may further include receiving second information from one or more second sensors associated with the vehicle based on the collision event. The second information may correspond to a set of health parameters associated with an occupant of the vehicle. Thereafter, the method may include controlling one or more medicament dispensers integrated into the vehicle based on at least one health parameter of the set of health parameters. Such dispensers may be controlled to dispense one or more medicaments on at least one body part of the occupant.

According to another embodiment of the disclosure, a vehicle is provided. The vehicle may include one or more medicament dispensers integrated into the vehicle. The vehicle may further include a circuitry communicably coupled to the one or more medicament dispensers. The circuitry may be configured to acquire first information from one or more first sensors associated with the vehicle. The first information may correspond to a collision event of the vehicle. The circuitry may be further configured to acquire second information from one or more second sensors associated with the vehicle based on the collision event. The second information may correspond to a set of health parameters associated with an occupant of the vehicle. Thereafter, the circuitry may be configured to control the one or more medicament dispensers based on at least one health parameter of the set of health parameters. Such dispensers may be controlled to dispense one or more medicaments on at least one body part of the occupant.

Figure 1:
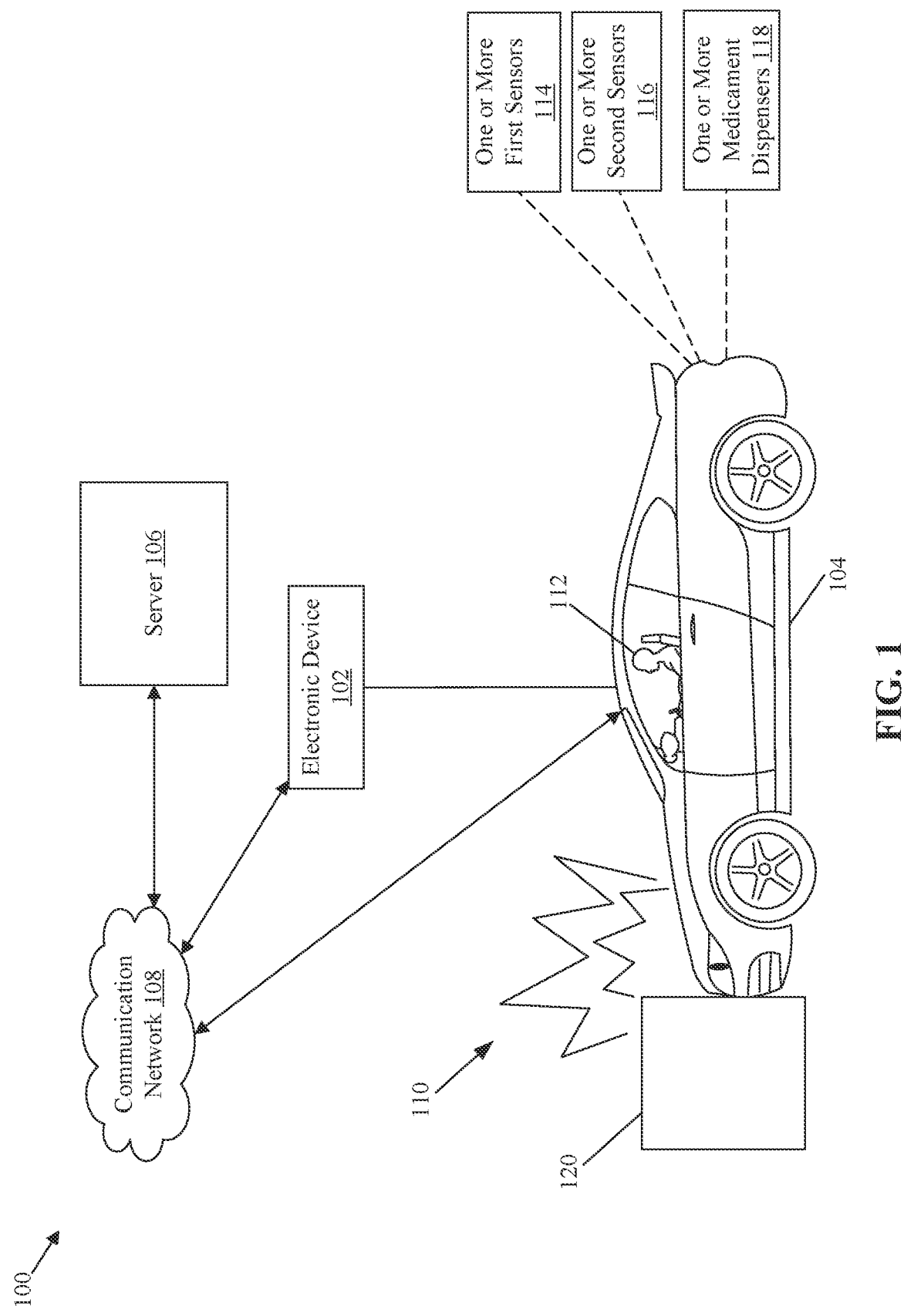
FIG. 1 is a block diagram that illustrates an exemplary network environment for control of a medicament dispenser based on a collision of a vehicle, in accordance with an embodiment of the disclosure.

The foregoing summary, as well as the following detailed description of the present disclosure, is better understood when read in conjunction with the appended drawings. For the purpose of illustrating the present disclosure, exemplary constructions of the preferred embodiment are shown in the drawings. However, the present disclosure is not limited to the specific methods and structures disclosed herein. The description of a method step or a structure referenced by a numeral in a drawing is applicable to the description of that method step or structure shown by that same numeral in any subsequent drawing herein.

DETAILED DESCRIPTION

The following described implementations may be found in an electronic device and method for control of a medicament dispenser integrated into a vehicle based on a collision of the vehicle. Exemplary aspects of the disclosure may provide an electronic device (such as a computer, a laptop, a mobile phone, a vehicle ECU, a smartphone, a smartwatch, and so on) that may be configured to receive first information from one or more first sensors (such as an impact detection sensor, a crash impact sound sensor, an accelerometer sensor, or a pressure sensor, and the like) associated with a vehicle. The first information may correspond to a collision event of the vehicle (for example, collision of the vehicle with an object such as a boulder, a vehicle, a tree, or a pavement). Based on the collision event, second information may be received from one or more second sensors (such as an image sensor, a position sensor, a blood pressure sensor, a heart rate sensor, a pulse rate sensor, a sound detection sensor, a weight sensor, or a temperature sensor, and the like) associated with the vehicle. The second information may correspond to a set of health parameters (such as a plurality of images of the occupant and a plurality of biological parameters such as a blood pressure, a heart rate, a pulse rate, a breath rate, a body weight, or a body temperature) associated with an occupant of the vehicle. Thereafter, based on at least one health parameter of the set of health parameters, one or more medicament dispensers integrated into the vehicle may be controlled to dispense one or more medicaments on at least one body part of the occupant.

One of the major issues with increased speed is the enhanced likelihood of vehicular accidents at higher speeds, which can result in minor to major injury and even the death of one or more occupants of the vehicle. To address the issue, vehicles are equipped with various safety measures (such as airbags, seatbelts, antilock brakes (ABS), traction control, brake assist, or collision warning) to reduce fatal injuries and loss of life. Existing safety measures installed in the vehicle may be useful in minor intensity impacts or collisions, but in high intensity impacts or collisions, they may not be as effective. In some cases, a high intensity collision of the vehicle, travelling at a high speed, with an object (such as a boulder, a car, a truck, or a wall) may result in an injury to one or more occupants of the vehicle. In some instances, the injury may even cause hemorrhage. The hemorrhage usually involves bleeding from an injured body part of one or more occupants of the vehicle in a short period of time. If left untreated, severe, or chronic hemorrhaging might lead to organ failure, seizures, coma, external bleeding, and eventually death.

The present disclosure provides an enhanced protection for occupants of a vehicle in case of a collision. The vehicle may be equipped with sensors to determine occurrence of a collision event, an intensity of the collision event, and a direction of the collision event. The vehicle may be further equipped with sensors to determine health parameters associated with the occupant(s) of the vehicle. The sensors may help to detect a location or an extent of an injury that the occupant may have received based on the collision event. To avoid injury complications or loss of life due to excessive bleeding or hemorrhage based on the collision event, one or more medicament dispensers may be integrated in the vehicle. Such dispensers may be used to dispense one or more medicaments on the injured body part of the occupant to reduce pain or blood loss associated with the injury. Further, the vehicle may be configured to access medical history information of the occupant and take remedial action based on the medical history of the occupant.

Reference will now be made in detail to specific aspects or features, examples of which are illustrated in the accompanying drawings. Wherever possible, corresponding, or similar reference numbers will be used throughout the drawings to refer to the same or corresponding parts.

FIG. 1 is a block diagram that illustrates an exemplary network environment for control of a medicament dispenser based on a collision of a vehicle, in accordance with an embodiment of the disclosure. With reference to FIG. 1, there is shown a network environment 100. The network environment 100 includes an electronic device 102, a vehicle 104, a server 106, and a communication network 108. In the network environment 100, there is further shown an occupant 112 of the vehicle 104, and a collision event 110 in which the vehicle 104 collides with an object 120. Further, in the network environment 100, there are shown one or more first sensors 114, one or more second sensors 116, and one or more medicament dispensers 118 associated with the vehicle 104. The electronic device 102, the vehicle 104, and the server 106 may communicate with each other via the communication network 108.

The electronic device 102 may include suitable logic, circuitry, interfaces, and/or code that may be configured to control and manage delivery of medicament to affected body parts from the one or more medicament dispensers 118 based on the collision event 110 of the vehicle 104. Examples of the electronic device 102 may include, but are not limited to, a computing device, a desktop, a personal computer, a laptop, a computer workstation, a tablet computing device, a smartphone, a cellular phone, a mobile phone, a smartwatch, a consumer electronic (CE) device having a display, a wearable display, a vehicle ECU, an in-vehicle display, or an edge device connected to a user's home network or an organization's network.

The vehicle 104 may include suitable logic, circuitry, interfaces, and/or code that may be configured to control and manage delivery of medicament to affected body parts from the one or more medicament dispensers 118 based on the collision event 110 of the vehicle 104. The vehicle 104 may be an electric vehicle that houses a battery unit such as a battery pack to power electrical components of the vehicle 104. The vehicle 104 may be a non-autonomous, a semi-autonomous, or an autonomous vehicle. The vehicle 104 may be a two-wheeler vehicle, a three-wheeler vehicle, a four-wheeler vehicle, a vehicle with any number of wheels, or a vehicle that uses one or more distinct renewable power sources such as solar power or hydrogen-based fuel. Examples of the vehicle 104 may include, but are not limited to, a hybrid electric vehicle (HEV), a battery electric vehicle (BEV), a plug-in hybrid electric vehicle (PHEV), or a vehicle with integrated photovoltaics or hydrogen fuel cells.

The server 106 may include suitable logic, circuitry, interfaces, and/or code that may be configured to receive first information corresponding to the collision event 110 and second information corresponding to a set of health parameters associated with the occupant 112 of the vehicle 104. The first information may be received from the one or more first sensors 114 associated with the vehicle 104 and the second information may be received from the one or more second sensors 116 associated with the vehicle 104. In accordance with an embodiment, the server 106 may control the one or more medicament dispensers 118 integrated into the vehicle 104 based on the collision event 110 and at least one health parameter of the set of health parameters to dispense one or more medicaments on at least one body part of the occupant 112.

The server 106 may execute operations through web applications, cloud applications, HTTP requests, repository operations, file transfer, and the like. Example implementations of the server 106 may include, but are not limited to, a database server, a file server, a web server, an application server, a mainframe server, a cloud computing server, or a combination thereof. In at least one embodiment, the server 106 may be implemented as a plurality of distributed cloud-based resources by use of several technologies that are well known to those ordinarily skilled in the art. A person with ordinary skill in the art will understand that the scope of the disclosure may not be limited to the implementation of the server 106 and the electronic device 102 as two separate entities or the server 106 and the vehicle 104 as two separate entities. In certain embodiments, the functionalities of the server 106 can be incorporated in its entirety or at least partially in the electronic device 102 or the vehicle 104, without a departure from the scope of the disclosure.

The server 106 may include a database that may be configured to store the first information and the second information. The database may be a relational database, a non-relational database, or a set of files in conventional or big-data storage. In some embodiments, the database may be hosted on a plurality of servers at same or different locations. Operations of the database may be executed using hardware including a processor, a microprocessor (e.g., to perform or control performance of one or more operations), a field-programmable gate array (FPGA), or an application-specific integrated circuit (ASIC). In some other instances, the database may be implemented using software. In an embodiment, the database may be stored or cached on a device, such as the server 106, the electronic device 102, or the vehicle 104. The device storing the database may be configured to control the one or more medicament dispensers 118 integrated into the vehicle 104 to dispense the one or more medicaments on the at least one body part of the occupant 112 based on the collision event 110 and the set of health parameters.

The communication network 108 may include a communication medium through which the electronic device 102, the vehicle 104, and the server 106 may communicate with each other. The communication network 108 may include one of a wired connection or a wireless connection. Examples of the communication network 108 may include, but are not limited to, the Internet, a cloud network, a Cellular or Wireless Mobile Network (such as a Long-Term Evolution and 5G New Radio), a Wireless Fidelity (Wi-Fi) network, a Personal Area Network (PAN), a Local Area Network (LAN), or a Metropolitan Area Network (MAN).

Various devices in the network environment 100 may be configured to connect to the communication network 108 in accordance with various wired and wireless communication protocols. Examples of such wired and wireless communication protocols may include, but are not limited to, at least one of a Transmission Control Protocol and Internet Protocol (TCP/IP), User Datagram Protocol (UDP), Hypertext Transfer Protocol (HTTP), File Transfer Protocol (FTP), Zig Bee, EDGE, IEEE 802.11, light fidelity (Li-Fi), 802.16, IEEE 802.11s, IEEE 802.11g, multi-hop communication, wireless access point (AP), device to device communication, cellular communication protocols, and Bluetooth (BT) communication protocols.

During operation, the electronic device 102 may receive the first information from one or more first sensors 114 (such as an impact detection sensor, a crash impact sound sensor, an accelerometer sensor, or a pressure sensor, and the like) associated with the vehicle 104. The first information may indicate a collision event of the vehicle 104. For example, the collision event may include a high-speed collision of the vehicle 104 with another vehicle or objects such as a boulder or a tree.

Based on the collision event, the electronic device 102 may receive (or request) second information from the one or more second sensors (such as an image sensor, a position sensor, a blood pressure sensor, a heart rate sensor, a pulse rate sensor, a sound detection sensor, a weight sensor, or a temperature sensor, and the like) associated with the vehicle 104. The second information may indicate a set of health parameters associated with the occupant 112 (such as a driver or a passenger) of the vehicle 104. The second information may include multimodal data such as a plurality of images of the occupant 112 from one or more viewpoints and a plurality of biological parameters or signals, including but not limited to, a blood pressure signal, a heart rate signal, a breath rate signal, a body weight signal, and a body temperature signal. Additionally, or alternatively, the second information may include indicators about a state of the occupant 112 (for example, conscious or unconscious), an amount of pain expressed by the occupant 112 through voice or face expression, and an extent of injury or blood loss.

Based on the second information (for example, at least one health parameter of the set of health parameters), the electronic device 102 may control the one or more medicament dispensers 118 (such as a sprayer, an atomizer, or a combination thereof) integrated into the vehicle 104 to dispense one or more medicaments (such as antihemorrhagic or hemostatic agents, antiseptics, or analgesic medications) on at least one body part (such as a forehead, chest, arm, or leg portion) of the occupant 112. Alternatively, the functions or operations executed by the electronic device 102, as described in FIG. 1, may be performed by the vehicle 104.

In an example embodiment, if the blood pressure of the occupant 112 is determined to be below a threshold (e.g., due to blood loss) and the occupant 112 is in an unconscious state with cut or laceration marks (e.g., potential spots with blood marks or clots) or burn marks on the body, then a medicament dispenser with a nozzle may be controlled to spray a defined volume of the medicament onto such marks on the body. Attributes such as a location, a size, and a type of each of such marks may be determined based on analysis of images included in the second information. The medicament dispenser 118 may include one or more actuators to align the nozzle with the location of the marks. The medicament may help to prevent further blood loss from an affected part of the body and may also help to alleviate the pain associated with such marks. Details related to the medicament dispenser 118 is provided in, for example, FIGS. 4, 5, and 6.

Figure 2:
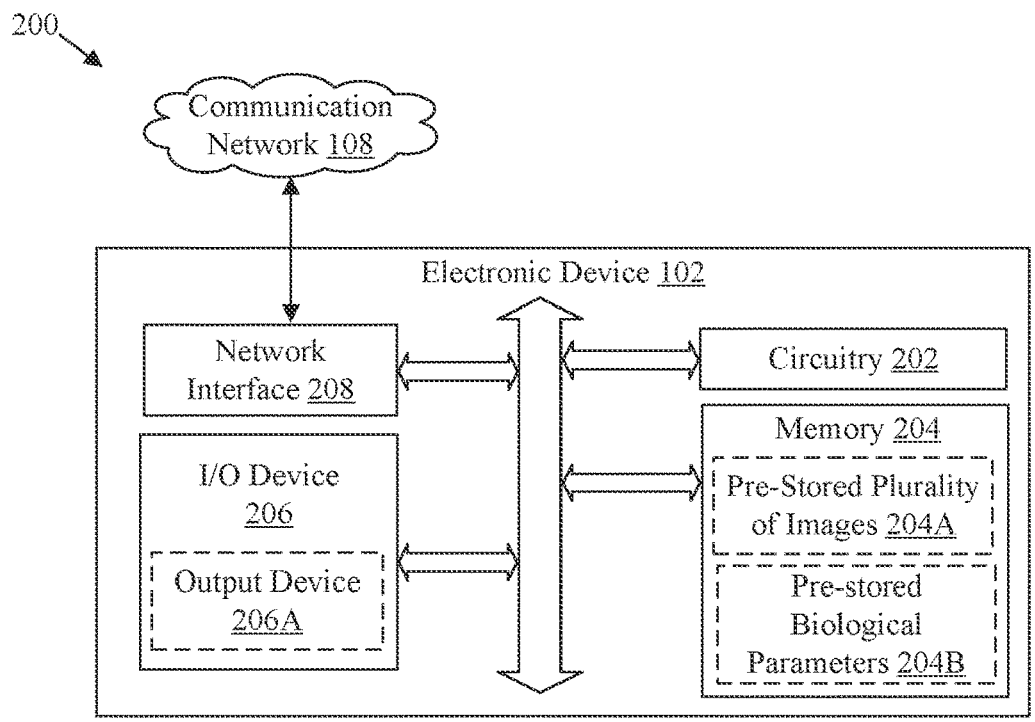
FIG. 2 is a block diagram that illustrates an exemplary electronic device of FIG. 1, in accordance with an embodiment of the disclosure.

FIG. 2 is a block diagram that illustrates an exemplary electronic device of FIG. 1. FIG. 2 is explained in conjunction with elements from FIG. 1. With reference to FIG. 2, there is shown a block diagram 200 of the electronic device 102. The electronic device 102 may include circuitry 202, a memory 204, an input/output (I/O) device 206, a display device 206A, and a network interface 208. In at least one embodiment, the I/O device 206 may also include the display device 206A. In at least one embodiment, the memory 204 may include a pre-stored plurality of images 204A and pre-stored biological parameters 204B. The circuitry 202 may be communicatively coupled to the memory 204, the I/O device 206, and the network interface 208 through a bus or an I/O interface of the electronic device 102. A person of ordinary skill in the art will understand that the block diagram 200 of the electronic device 102 may also include other suitable components or systems, in addition to the components or systems which are illustrated herein to describe and explain the function and operation of the present disclosure. Detailed description of such components or systems has been omitted from the disclosure for the sake of brevity.

The circuitry 202 may include suitable logic, circuitry, and/or interfaces code that may be configured to execute program instructions associated with different operations to be executed by the electronic device 102. The circuitry 202 may include one or more specialized processing units, which may be implemented as a separate processor. In an embodiment, the one or more specialized processing units may be implemented as an integrated processor or a cluster of processors that perform the functions of the one or more specialized processing units, collectively. For example, the circuitry 202 may include a microprocessor, a microcontroller, a digital signal processor (DSP), an application-specific integrated circuit (ASIC), a Field-Programmable Gate Array (FPGA), or any other digital or analog circuitry configured to interpret and/or to execute program instructions and/or to process data. Examples of the circuitry 202 may include a Central Processing Unit (CPU), a Graphical Processing Unit (GPU), an x86-based processor, an x64-based processor, a Reduced Instruction Set Computing (RISC) processor, a Complex Instruction Set Computing (CISC) processor, and/or other hardware processors. The functions or operations executed by the electronic device 102, as described in FIG. 1, may be performed by the circuitry 202. Operations executed by the circuitry 202 are described in detail, for example, in FIGS. 4, 5, 6, and 8.

The memory 204 may include suitable logic, circuitry, interfaces, and/or code that may be configured to store the program instructions executable by the circuitry 202. In at least one embodiment, the memory 204 may be configured to store the pre-stored plurality of images 204A and the pre-stored biological parameters 204B. The memory 204 may be a persistent storage medium, a non-persistent storage medium, or a combination thereof. Example implementations of the memory 204 may include, but are not limited to, Random Access Memory (RAM), Read Only Memory (ROM), Hard Disk Drive (HDD), a Solid-State Drive (SSD), a CPU cache, and/or a Secure Digital (SD) card.

The I/O device 206 may include the display device 206A. The display device 206A may include suitable logic, circuitry, and interfaces that may be configured to receive inputs from the circuitry 202 to render, on a display screen, first aid information based on the set of health parameters. The first aid information corresponds to a medical assistance for the at least one body part of the occupant. The first aid information may be saved in the memory 204, the server 106 or the database associated with the server 106. The display device 206A may be a touch screen which may enable a user to provide a user-input via the display device 206A. The touch screen may be at least one of a resistive touch screen, a capacitive touch screen, or a thermal touch screen. The display device 206A may be realized through several known technologies such as, but not limited to, at least one of a Liquid Crystal Display (LCD) display, a Light Emitting Diode (LED) display, a plasma display, or an Organic LED (OLED) display technology, or other display devices. In accordance with an embodiment, the display device 206A may refer to a display screen of the smartphone, the computer workstation, the handheld computer, the cellular/mobile phone, the smartwatch, the portable consumer electronic (CE) device, a smart-glass device, a see-through display, a projection-based display, an electro-chromic display, or a transparent display.

The network interface 208 may include suitable logic, circuitry, and interfaces that may be configured to facilitate communication between the electronic device 102, and the various devices or components of the network environment 100 (such as the vehicle 104 and the server 106) via the communication network 108. The network interface 208 may be implemented by use of various known technologies to support wired or wireless communication of the server 106 with the communication network 108. The network interface 208 may include, but is not limited to, an antenna, a radio frequency (RF) transceiver, one or more amplifiers, a tuner, one or more oscillators, a digital signal processor, a coder-decoder (CODEC) chipset, a subscriber identity module (SIM) card, or a local buffer circuitry. The network interface 208 may be configured to communicate via wireless communication with networks, such as the Internet, an Intranet, or a wireless network, such as a cellular telephone network, a wireless local area network (LAN), and a metropolitan area network (MAN). The wireless communication may be configured to use one or more of a plurality of communication standards, protocols and technologies, such as Global System for Mobile Communications (GSM), Enhanced Data GSM Environment (EDGE), wideband code division multiple access (W-CDMA), Long Term Evolution (LTE), $5^{th}$ Generation (5G) New Radio (NR), code division multiple access (CDMA), time division multiple access (TDMA), Bluetooth, Wireless Fidelity (Wi-Fi) (such as IEEE 802.11a, IEEE 802.11b, IEEE 802.11g or IEEE 802.11n), voice over Internet Protocol (VOIP), light fidelity (Li-Fi), Worldwide Interoperability for Microwave Access (Wi-MAX), a near field communication protocol, a wireless pear-to-pear protocol, a protocol for email, instant messaging, and a Short Message Service (SMS).

Figure 3:
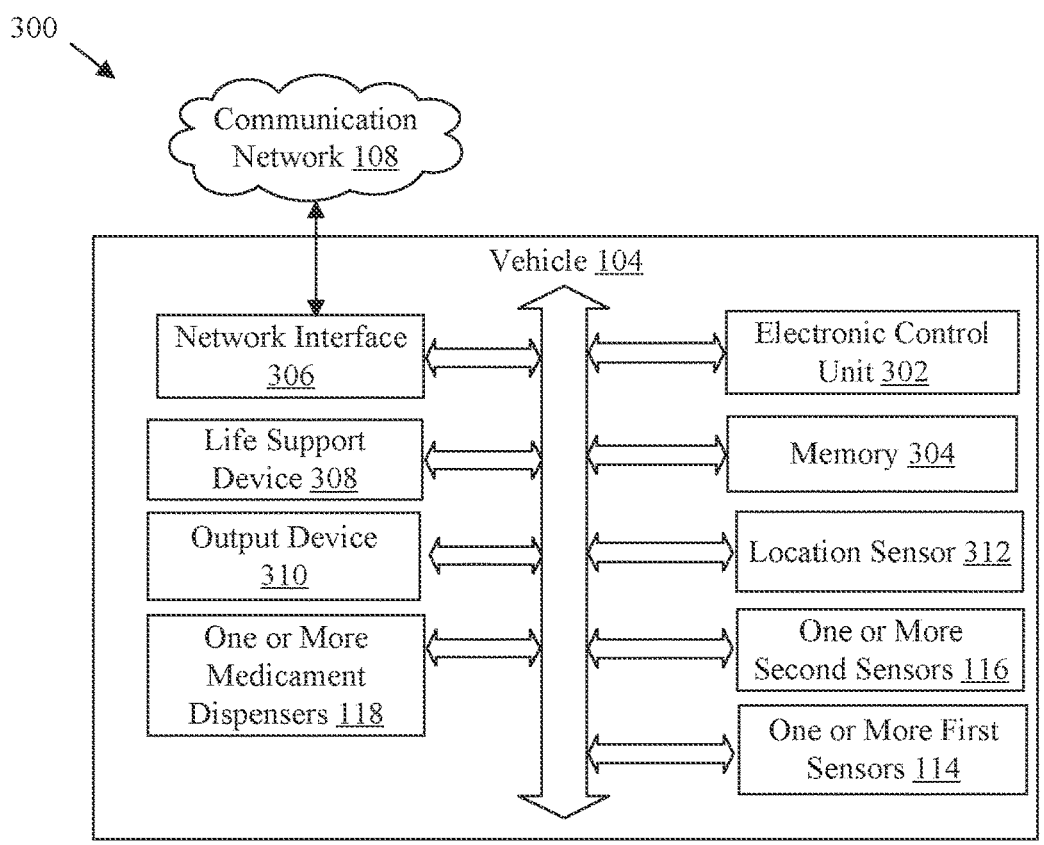
FIG. 3 is a block diagram that illustrates an exemplary vehicle of FIG. 1, in accordance with an embodiment of the disclosure.

FIG. 3 is a block diagram that illustrates an exemplary vehicle of FIG. 1. FIG. 3 is explained in conjunction with elements from FIG. 1 and FIG. 2. With reference to FIG. 3, there is shown a block diagram 300 of the vehicle 104. The vehicle 104 may include an electronic control unit 302, a memory 304, a network interface 306, a life support device 308, an output device 310, a location sensor 312, the one or more first sensors 114, the one or more second sensors 116, and the one or more medicament dispensers 118.

The electronic control unit 302 may include suitable logic, circuitry, interfaces, and/or code that may be configured to monitor a usage of the vehicle 104. The electronic control unit 302 may be a specialized electronic circuitry that may include an electronic control unit (ECU) processor to control different functions, such as, but not limited to, engine operations, communication operations, and data acquisition of the vehicle 104. The electronic control unit 302 may store information associated with the vehicle 104 and may transmit such information to the electronic device 102 or server 106 based on requirements. In an embodiment, the electronic control unit 302 may determine the collision event 110 of the vehicle 104. One example implementation of the electronic control unit 302 can be a microprocessor. Other examples of the electronic control unit 302 may include, but are not limited to, a vehicle control system, an in-vehicle infotainment (IVI) system, an automotive Head-up Display (HUD), an automotive dashboard, an embedded device, a smartphone, a human-machine interface (HMI), a computer workstation, a handheld computer, a cellular/mobile phone, a portable CE device, a server, and other computing devices.

The memory 304 may include suitable logic, circuitry, interfaces, and/or code that may be configured to store a set of instructions executable by the electronic control unit 302. The set of instructions may be executed by the electronic control unit 302 to perform operations of the electronic control unit 302. In at least one embodiment, the memory 304 may be configured to store the pre-stored plurality of images 204A and the pre-stored biological parameters 204B associated with the occupant 112 of the vehicle 104. The memory 304 may be a persistent storage medium, a non-persistent storage medium, or a combination thereof. Example implementations of the memory 304 may include, but are not limited to, RAM, ROM, a HDD, an SSD, a CPU cache, and/or a SD card.

The network interface 306 may include suitable logic, circuitry, and interfaces that may be configured to facilitate communication between the electronic control unit 302 and the various devices or components of the network environment 100 (such as the electronic device 102 and/or the server 106), via the communication network 108. The network interface 306 may be implemented by use of various known technologies to support wired or wireless communication of the vehicle 104 with the communication network 108. The network interface 306 may include, but is not limited to, an antenna, a RF transceiver, one or more amplifiers, a tuner, one or more oscillators, a digital signal processor, a CODEC chipset, a SIM card, or a local buffer circuitry. The network interface 306 may be configured to communicate via wireless communication with networks, such as the Internet, an Intranet, or a wireless network, such as a cellular telephone network, a wireless LAN, and a MAN. The wireless communication may be configured to use one or more of a plurality of communication standards, protocols, and technologies, such as GSM, EDGE, W-CDMA, LTE, 5G NR, CDMA, TDMA, Bluetooth, Wi-Fi (such as IEEE 802.11a, IEEE 802.11b, IEEE 802.11g or IEEE 802.11n), VoIP, Li-Fi, Wi-MAX, a protocol for email, instant messaging, and a SMS.

The network interface 306 may include a medium through which the electronic control unit 302, the memory 304, the one or more first sensors 114, the one or more second sensors 116, the one or more medicament dispensers 118, the life support device 308, the output device 310, and the location sensor 312 may communicate with each other. In accordance with an embodiment, in-vehicle communication of audio/video data may occur by use of Media Oriented Systems Transport (MOST) multimedia network protocol of the network interface 306 or other suitable network protocols for vehicle communication. The MOST-based network may be a separate network from the controller area network (CAN). The MOST-based network may use a plastic optical fiber (POF) medium. In accordance with an embodiment, the MOST-based network, the CAN, and other in-vehicle networks may co-exist in a vehicle, such as the vehicle 104. The network interface 306 may facilitate access control and/or communication between the electronic control unit 302 and other ECUs, such as ECM or a telematics control unit of the vehicle 104.

Various devices or components in the vehicle 104 may connect to the network interface 306, in accordance with various wired and wireless communication protocols. Examples of the wired and wireless communication protocols for the network interface 306 may include, but are not limited to, cellular Vehicle-to-Everything (C-V2X) communication, Dedicated Short-Range Communication (DSRC), a vehicle area network (VAN), a CAN bus, Domestic Digital Bus (D2B), Time-Triggered Protocol (TTP), FlexRay, IEEE 1394, Carrier Sense Multiple Access With Collision Detection (CSMA/CD) based data communication protocol, Inter-Integrated Circuit ($I^2C$), Inter Equipment Bus (IEBus), Society of Automotive Engineers (SAE) J1708, SAE J1939, International Organization for Standardization (ISO) 11992, ISO 11783, MOST, MOST25, MOST50, MOST150, Plastic optical fiber (POF), Power-line communication (PLC), Serial Peripheral Interface (SPI) bus, and/or Local Interconnect Network (LIN).

The life support device 308 may include, for example, at least one of a defibrillator, a cardiopulmonary resuscitation (CPR) device, or a breathing support device. The defibrillator may be a device that sends an electric pulse or shock to the heart to restore a normal heartbeat. They may be used to prevent or correct an arrhythmia or an uneven heartbeat that is too slow or too fast. If the heart suddenly stops, the defibrillator may help to revive the heartbeat. For example, if due to the collision event 110, the heartbeat of the occupant 112 stops or drops too low, then the defibrillator may be used restore the heartbeat of the occupant 112. The CPR device may provide chest compression during cardiac arrest. The CPR device is also known as automated chest compression device, and primarily refers to a load-distributing band device and a pneumatic piston device. The breathing support device may help to push air into lungs. The person may wear a mask or nasal plugs that may be connected to the breathing support device. The breathing support device may supply pressurized air into the airways. For example, if the occupant 112 of the vehicle 104 is facing an abnormal breathing problem, then the breathing support device may be used to provide an assistive breathing support.

The output device 310 may include suitable logic, circuitry, and interfaces that may be configured to receive inputs or signals to render, on a display screen, first aid information based on the set of health parameters. The first aid information may be a form of a medical assistance for at least one body part of the occupant 112. The first aid information may be saved in the memory 204, the memory 304, or the database associated with the server 106. The output device 310 may be a touch screen which may enable a user (such as the occupant 112 of the vehicle 104) to provide a user-input via the output device 310. The output device 310 may be realized through several known technologies such as, but not limited to, at least one of a Liquid Crystal Display (LCD) display, a Light Emitting Diode (LED) display, a plasma display, or an Organic LED (OLED) display technology, or other output devices. In accordance with an embodiment, the output device 310 may refer to a display screen of the smartphone, an infotainment system of the vehicle, the computer workstation, the handheld computer, the cellular/mobile phone, the portable consumer electronic (CE) device, a smart-glass device, a see-through display, a projection-based display, an electrochromic display, or a transparent display.

The location sensor 312 may include suitable logic, circuitry, and/or interfaces that may be configured to determine a current geo-location of the vehicle 104. Examples of the location sensor 312 may include, but are not limited to, a Global Navigation Satellite System (GNSS)-based sensor of the vehicle 104. Examples of the GNSS-based sensor may include, but are not limited to, global positioning sensor (GPS), Global Navigation Satellite System (GLONASS), or other regional navigation systems or sensors.

Figure 4:
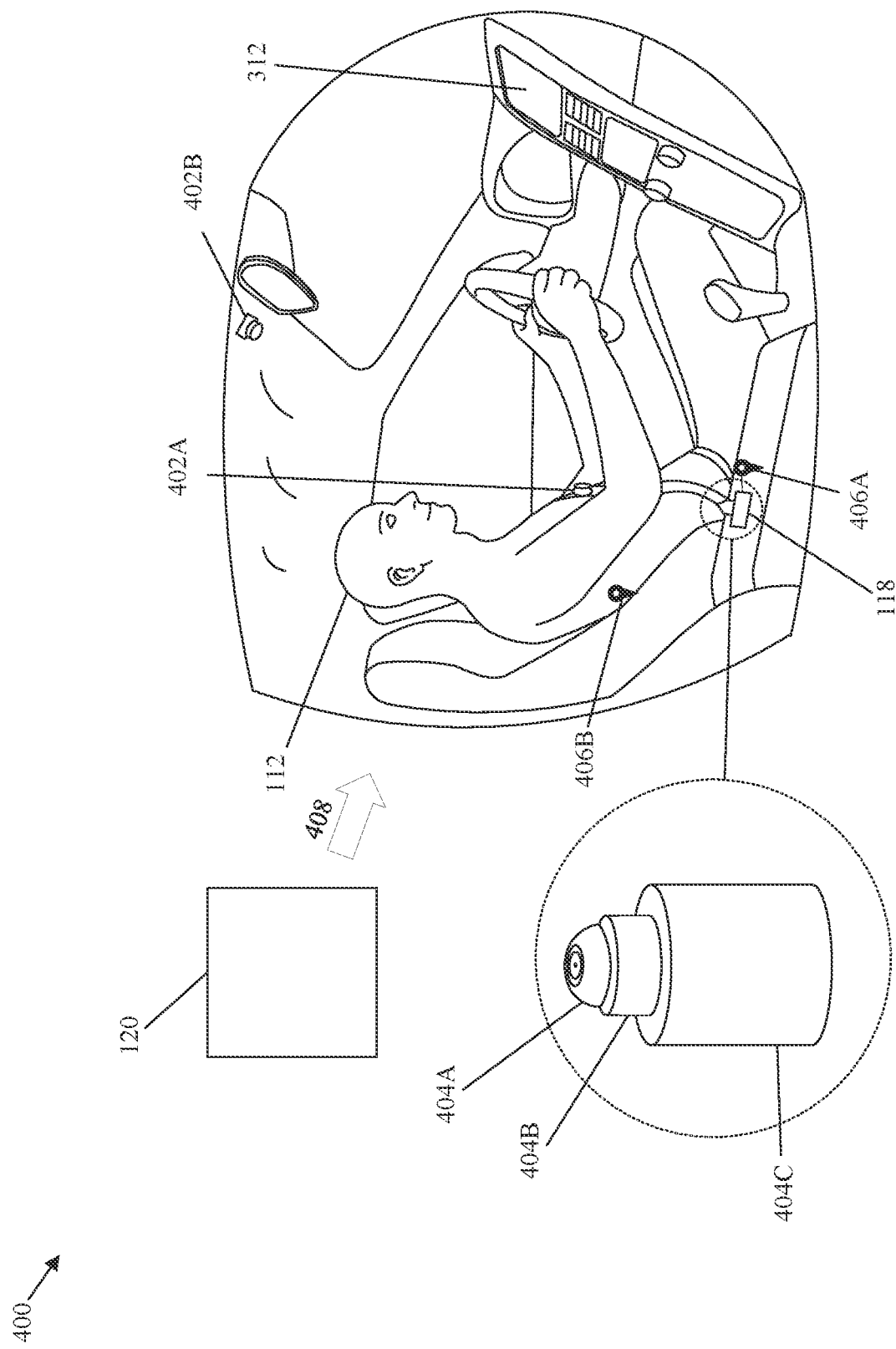
FIG. 4 is a diagram that illustrates an exemplary representation of a vehicle in a collision event, in accordance with an embodiment of the disclosure.

FIG. 4 is a diagram that illustrates an exemplary representation of a vehicle in a collision event. FIG. 4 is explained in conjunction with elements from FIGS. 1, 2, and 3. With reference to FIG. 4, there is shown an exemplary scenario 400 of the collision event 110 associated with the vehicle 104. In the scenario 400, there is shown a view of a passenger compartment of the vehicle 104. As illustrated, the vehicle 104 collides with the object 120 at a time instant (Tc). The functions or operations are described as being executed by the circuitry 202, but, alternatively, may be performed by the electronic control unit 302.

In an embodiment, the circuitry 202 may receive the first information from one or more first sensors 114 (such as an impact detection sensor, a crash impact sound sensor, an accelerometer sensor, or a pressure sensor) associated with the vehicle 104. The first information may correspond to the collision event 110, an intensity of the collision, and a direction of the collision (such as a direction 408). After the reception of the first information, the circuitry 202 may analyze the first information to determine a positive occurrence of the collision of the vehicle 104 (for example, a collision between the vehicle 104 and the object 120), the direction of the collision (for example, the direction of the collision may be towards a front portion, a back portion, or a side portion of the vehicle 104), and the intensity of the collision (for example, a force with which the vehicle 104 collided with the object 120).

Based on the positive occurrence of the collision of the vehicle 104, the circuitry 202 may receive the second information from the one or more second sensors 116 (such as a sensor 402A and a sensor 402B). In an embodiment, the sensor 402A may be at least one of a position sensor for determining a position of the occupant 112 in the vehicle 104, a blood pressure sensor for determining a blood pressure of the occupant 112, a heart rate sensor for determining a heart rate of the occupant 112, a pulse rate sensor for determining a pulse rate of the occupant 112, a sound detection sensor for determining a breath rate of the occupant 112, a weight sensor for determining a body weight of the occupant 112, or a temperature sensor determining a body temperature of the occupant 112. The sensor 402B may be an image sensor, such as digital type electronic imaging devices like digital cameras, imaging tools used in medical, camera modules, night vision tools like radar, thermal imaging devices, and sonar, for acquiring a plurality of images of the occupant 112.

The second information may be received until a predefined time-period (for example, 3 seconds) from a time of the collision event 110. The second information may correspond to a set of health parameters associated with the occupant 112 of the vehicle 104. For example, the set of health parameters may include a first set of health parameters and a second set of health parameters. The first set of health parameters may relate to a plurality of images of the occupant 112 at the time of the collision event 110, and the second set of health parameters may relate to a plurality of biological parameters of the occupant 112 at the time of the collision event 110. In an exemplary embodiment, the biological parameters may relate to at least one of a blood pressure, a heart rate, a pulse rate, a breath rate, a body weight, or a body temperature of the occupant 112.

Based on reception of the second information, the circuitry 202 may be configured to control the one or more medicament dispensers 118 integrated into the vehicle 104 to dispense one or more medicaments on at least one body part of the occupant 112. For example, when the vehicle 104 collides or crashes with the object 120, the circuitry 202 may determine a status of the occupant 112 and whether the occupant 112 has received any injury due to the collision. Based on a determination of an injured body part of the occupant 112, the circuitry 202 may control (such as an operation to start or stop a dispensation of medicaments) the one or more medicament dispensers 118 to dispense one or more medicaments on the determined injured body part of the occupant 112. In FIG. 4, only one medicament dispenser is illustrated as an example, but such an example should not be construed as limiting the disclosure. In certain embodiments, the vehicle 104 may include a plurality of the medicament dispensers, without departing from the scope of the present disclosure. For example, a medicament dispenser may be placed close to each seat in the vehicle 104.

Each medicament dispenser may include a medicament reservoir 404C integrated or installed in the vehicle 104. For example, the medicament reservoir 404C may be located at a first location 406A (e.g., in a center console in the vehicle 104). The medicament reservoir 404C may be configured to store a medicament of the one or more medicaments. In an embodiment, the medicament reservoir 404C may include a plurality of medicaments, each of which may be stored in a separate isolated chamber within the medicament reservoir 404C. In some embodiments, each of the one or more medicament dispensers 118 may include a nozzle 404A integrated in the vehicle 104 and communicably coupled to the medicament reservoir 404C to dispense the medicament. The nozzle 404A may be positioned at the first location 406A, which may be proximal to a second location 406B of the occupant 112. In other embodiments, the nozzle 404A and the medicament reservoir 404C may not be coupled to each other and may be at different locations in the vehicle 104 as opposed to the illustration in the FIG. 4, without departing from the scope of the present disclosure. For example, the nozzle 404A and/or medicament reservoir 404C may be located in various areas of the vehicle 104, such as the center console, seat, armrest, door, dashboard, or ceiling, and the like.

Each of the one or more medicament dispensers 118 may include an actuator 404B communicably coupled to the nozzle 404A and the medicament reservoir 404C. The circuitry 202 may be configured to control the actuator 404B to release the medicament from the medicament reservoir 404C on at least one body part of the occupant 112, via the nozzle 404A. In an embodiment, the circuitry 202 may be configured to control, after a completion of the predefined time-period, the actuator 404B to regulate an amount of the medicament on at least one body part of the occupant 112. The medicament may be dispensed from the nozzle in the form of a spray, for example.

Figure 5:
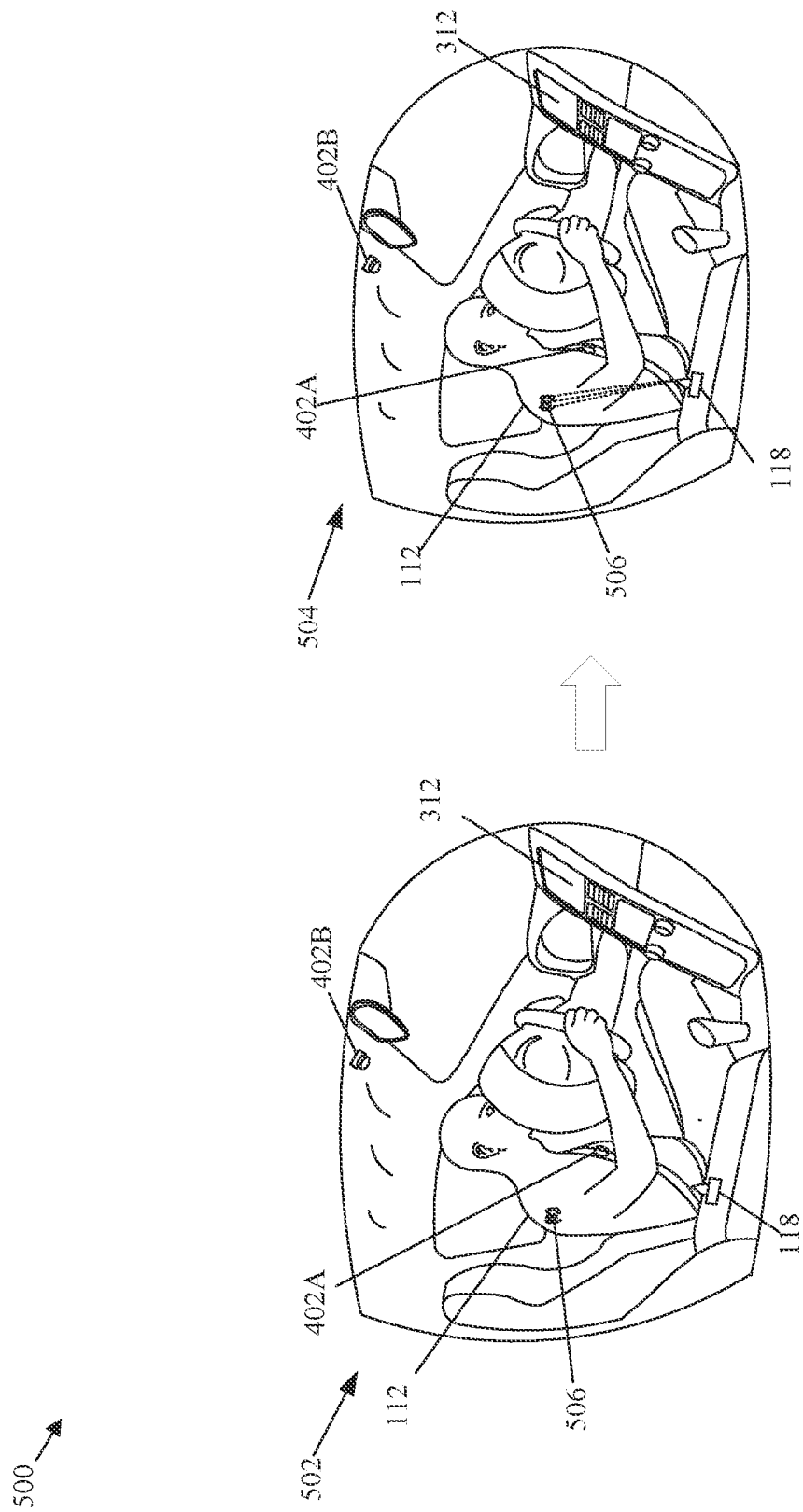
FIG. 5 is a diagram that illustrates a view of a passenger compartment of a vehicle at two different time instants after a collision event, in accordance with an embodiment of the disclosure.

FIG. 5 is a diagram that illustrates a view of a passenger compartment of a vehicle at two different time instants after a collision event. FIG. 5 is explained in conjunction with elements from FIGS. 1, 2, 3, and 4. With reference to FIG. 5, there is shown a diagram 500 that illustrates a view of a passenger compartment of the vehicle 104 at two different time instants 502 and 504 associated with the collision event 110.

At a first time instant 502, a first set of health parameters that may relate to a plurality of images of the occupant in the collision event 110 may be analyzed. As part of the analysis, the circuitry 202 may compare the plurality of images of the occupant 112 with the pre-stored plurality of images 204A of the occupant 112. The pre-stored plurality of images 204A may be captured by the one or more second sensors 116 (such as the sensor 402B) in an event different from the collision event 110. For example, the sensor 402B may capture a plurality of images of the occupant 112 a few minutes before the vehicle 104 crashes or collides with the object 120. Such images may be stored in the memory 204, the memory 304, or a database on the server 106 and may be considered as the pre-stored plurality of images 204A. Based on the comparison, the circuitry 202 may determine at least one body part of the occupant that requires an immediate medical attention or a medical intervention. For example, after collision of the vehicle 104 with the object 120, the occupant 112 may receive an injury on a body part 506 of the occupant 112.

In accordance with an embodiment, the circuitry 202 may compare a second set of health parameters that may relate a plurality of biological parameters of the occupant 112 (acquired at the time of the collision event 110) with the pre-stored biological parameters 204B of the occupant 112. The pre-stored biological parameters 204B may be measured by the one or more second sensors 116 (such as the sensor 402A) in an event different from the collision event 110. For example, the sensor 402A may measure the biological parameters of the occupant 112 a few minutes before the vehicle 104 collides or crashes with the object 120. The measured biological parameters may be pre-stored in the memory 204, the memory 304, or a database on the server 106 as the pre-stored biological parameters 204B. Based on the comparison, the circuitry 202 may be configured to determine at least one body part of the occupant (such as a body part 506) that requires an immediate medical attention or a medical intervention. For example, after collision of the vehicle 104 with the object 120, the occupant 112 may receive cuts on the body part 506. The cuts may need a medicament to prevent excess blood loss.

At a second time instant 504, the circuitry 202 may control the one or more medicament dispensers 118 to regulate an amount of one or more medicaments on the at least one body part (such as the body part 506) of the occupant 112. For example, based on the determination that at least one body part of the occupant 112 requires immediate medication attention or medical intervention, the circuitry 202 may control the actuator 404B to release the medicament from the medicament reservoir 404C on the body part 506 of the occupant 112 via the nozzle 404A.

Figure 6:
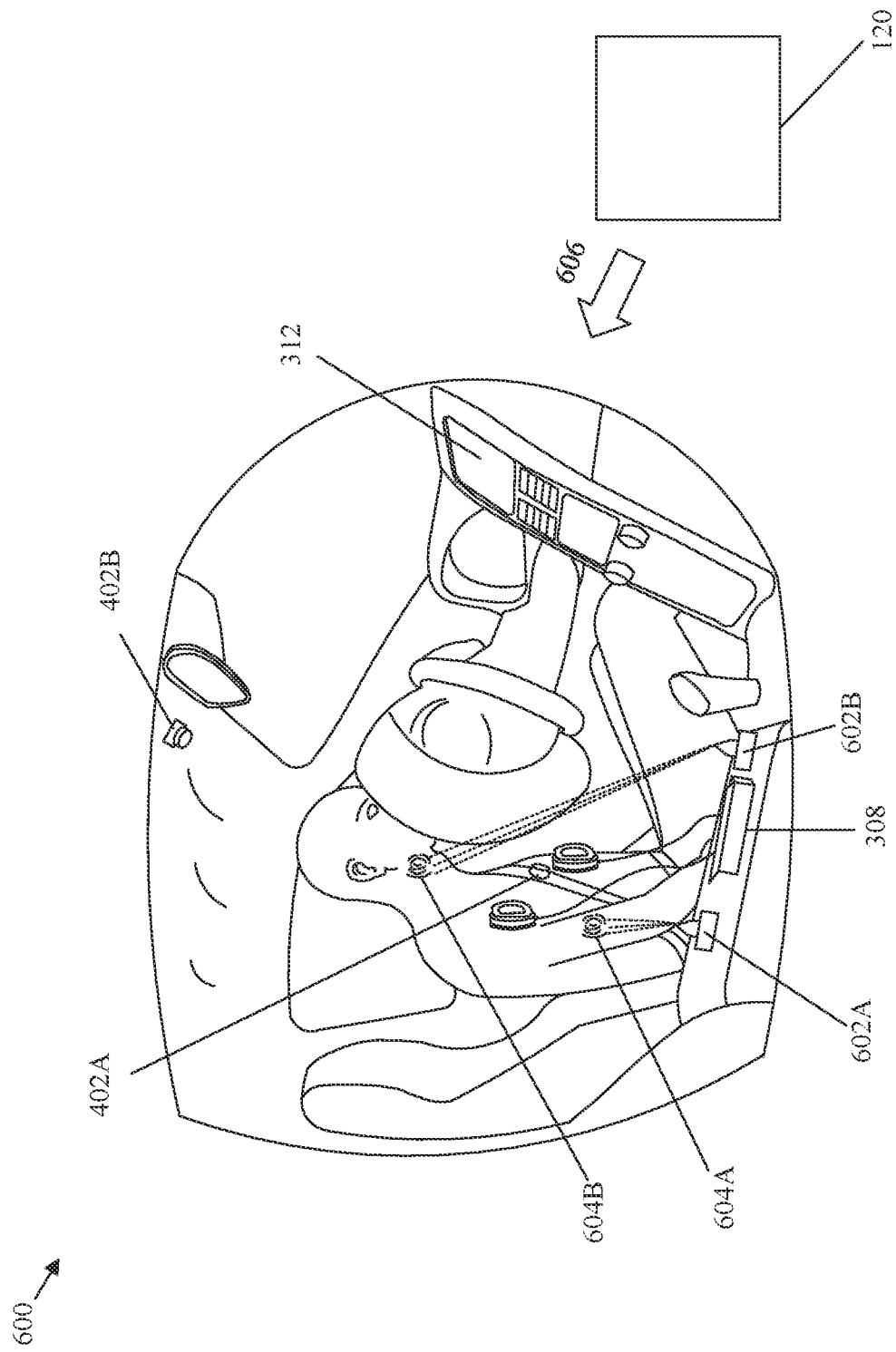
FIG. 6 is a diagram that illustrates an exemplary collision event associated with a vehicle, in accordance with an embodiment of the disclosure.

FIG. 6 is a diagram that illustrates an exemplary collision event associated with a vehicle. FIG. 6 is explained in conjunction with elements from FIGS. 1, 2, 3, 4, and 5. With reference to FIG. 6, there is shown a diagram 600 that includes a view of a passenger compartment at the time of the collision event 110 in which the vehicle 104 crashes or collides with the object 120 from a direction 606. The vehicle 104 includes medicament dispensers (such as a medicament dispenser 602A and a medicament dispenser 602B) positioned close to a seat of the occupant 112.

During operation, the circuitry 202 may receive the first information from the one or more first sensors 114 (such as the impact detection sensor) associated with the vehicle 104. The first information may correspond to a direction such as the direction 606 of the collision. For example, based on the first information received from the impact detection sensor, the circuitry 202 may determine the collision event 110 and the direction of collision as the direction 606. Based on the direction 606, the circuitry 202 may control the actuator 404B to regulate an amount of the medicament that needs to be applied on at least one body part (such as a first body part 604A and a second body part 604B) of the occupant 112. In a situation where the direction of collision is along a direction of movement of the vehicle 104, the strength of the collision may be less as compared to a situation in which the direction of collision is opposite to the direction of movement of the vehicle 104. In the former situation, the occupant 112 may receive less serious injuries (e.g., a bruise on a shoulder portion of the occupant 112) as compared to the latter situation in which the occupant 112 may receive more serious cuts or bruises on parts of the body (such as parts 604A and 604B).

In accordance with an embodiment, the amount of the medicament to be dispensed by the one or more medicament dispensers 118 (such as the medicament dispensers 602A and 602B) may not just depend on the collision (such as the direction 606). Other factors such as a state of occupant (e.g., a conscious state, an inebriated state, a drugged state, or a unconscious state), an existing medical condition (such as a physical disability or epilepsy), occupant's age, occupant's pregnancy stage, occupant's gender, a number and location of occupants in the vehicle 104, or a number of children in the vehicle 104 may be relied on to prioritize a dispensation of the medicament among several occupants of the vehicle 104 and define a volume (i.e., a quota) of the medicament for each occupant of the vehicle 104. The number of injuries and the severity of the injuries of the occupant(s) of the vehicle may also determine the amount of the medicament to be dispensed to the occupants(s). For example, a larger portion of the medicament may be reserved for an occupant in the driver seat of the vehicle 104, who is unconscious and has several laceration marks, followed by smaller portions for other adults or children in the vehicle 104.

In accordance with an embodiment, the one or more medicament dispensers (such as the medicament dispensers 602A and 602B) may be communicably coupled to the life support device 308 that may be integrated into the vehicle 104. The life support device 308 may be configured to be coupled to a body part of the occupant 112 based on a human input or a robotic mechanism. Based on the at least one health parameter of the set of health parameters, the circuitry 202 may control the life support device 308 to facilitate a recovery of a body part of the occupant 112 that is injured (or requires a medical intervention). For example, after the collision event 110, it may be determined that the heartbeat of the occupant 112 is low (i.e., below a minimum heartbeat value required for a healthy function of the heart) or is close to zero based on the set of health parameters. In such a case, the circuitry 202 may control the life support device 308 (such as a defibrillator as illustrated) to revive the heart of the occupant 112. By way of example, and not limitation, the life support device 308 may include at least one of a defibrillator, a cardiopulmonary resuscitation (CPR) device, or a breathing support device.

Figure 7:
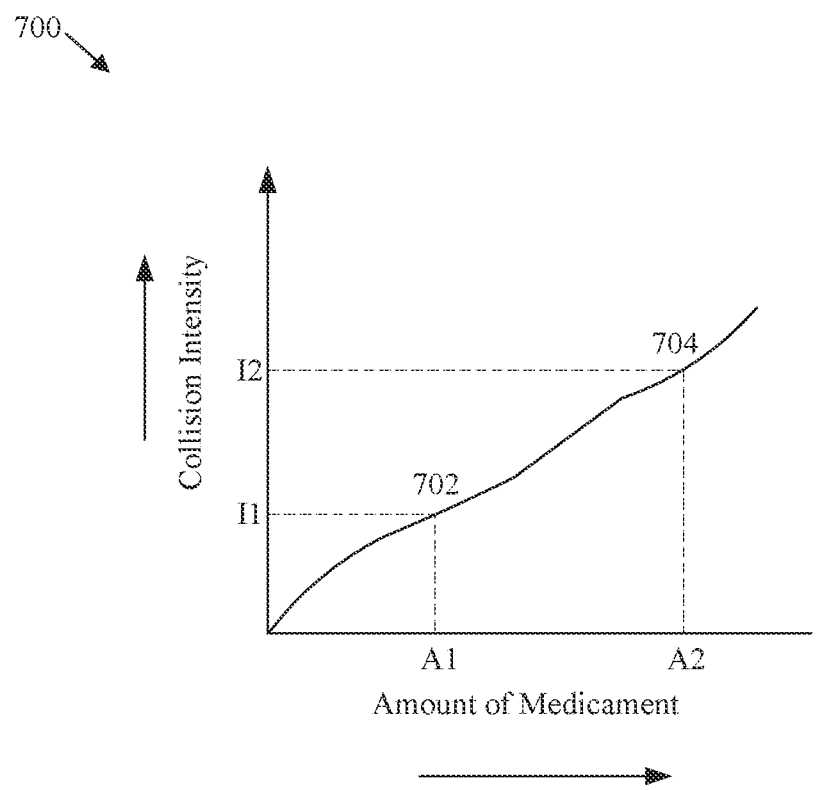
FIG. 7 is a diagram that illustrates a relationship between a collision intensity and an amount of medicament, in accordance with an embodiment of the disclosure.

FIG. 7 is a diagram that illustrates a relationship between a collision intensity and an amount of medicament, in accordance with an embodiment of the disclosure. FIG. 7 is explained in conjunction with elements from FIGS. 1, 2, 3, 4, 5, and 6. With reference to FIG. 7, there is shown a graph 700 that illustrates a relationship between a collision intensity and an amount of medicament dispensed after the collision of the vehicle 104. From the graph 700, it may be observed that the intensity of the collision is I1 at 702 and the amount of the medicament dispensed is A1. Similarly, the intensity of the collision is I2 at 704 and the amount of the medicament dispensed is A2. Thus, from the graph 700, it can be inferred that a dispensation volume (i.e., an amount volume of the medicament) may linearly increase (or linearly decrease) with an increase (or a decrease) in the intensity of the collision. The data presented in the graph 700 is merely an example and the example should not be construed as limiting the disclosure. In certain embodiments, the relationship between the collision intensity and the amount of medicament dispensed after the collision of the vehicle 104 may be a non-linear relationship.

In accordance with an embodiment, the first information from the one or more first sensors 114 may correspond to an intensity of the collision event 110. Based on the intensity of the collision event 110, the circuitry 202 may be configured to control the actuator 404B to regulate an amount of one or more medicaments that may need to be applied on the at least one body part (such as parts 506, 604A, or 604B) of the occupant 112.

Figure 8:
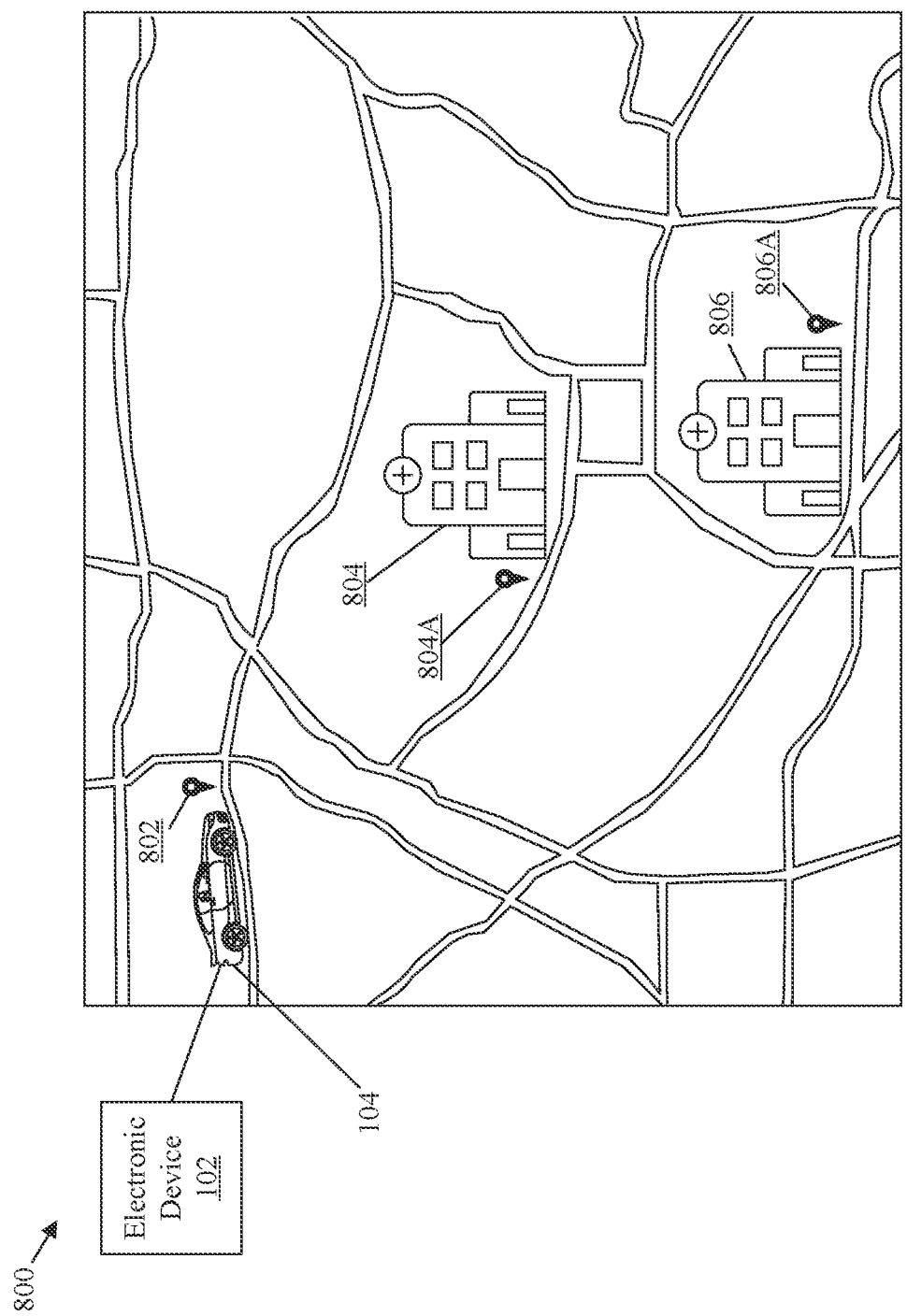
FIG. 8 is a diagram that illustrates an exemplary scenario of a medicament dispensation based on a location of the vehicle, in accordance with an embodiment of the disclosure.

FIG. 8 is a diagram that illustrates an exemplary scenario of a medicament dispensation based on a location of the vehicle, in accordance with an embodiment of the disclosure. FIG. 8 is explained in conjunction with elements from FIGS. 1, 2, 3, 4, 5, 6, and 7. With reference to FIG. 8, there is shown an exemplary scenario diagram 800. In the scenario diagram 800, there is shown a map of a region with a plurality of the medical facilities (such as a first medical facility 804 and a second medical facility 806) and a user interface element (e.g., a car icon) to represent a geographic location 802 of the vehicle 104 at a particular time instant. The location of each medical facility may be indicated via a user interface element (e.g., an icon) on the map.

During operation, the circuitry 202 may be configured to receive third information that may correspond to the geographic location 802 of the vehicle 104. Based on the geographical location 802 of the vehicle 104, the circuitry 202 may determine a medical facility from the plurality of the medical facilities (such as medical facilities 804 and 806) which may be at a first distance from the geographic location 802 of the vehicle 104. As illustrated, the first medical facility 804 may be present at a location 804A and the second medical facility 806 may be present at a location 806A. Information associated with the location 804A of the first medical facility 804 and the location 806A of the second medical facility 806 may be already stored on the server 106, in the memory 204 of the electronic device 102, or in the memory 304 of the vehicle 104. Based on the received third information, the circuitry 202 may control the one or more medicament dispensers 118 to regulate an amount of one or more medicaments on at least one body part of the occupant 112.

In accordance with an embodiment, the circuitry 202 may receive the information associated with the location 804A of the first medical facility 804 and the location 806A of the second medical facility 806 from the server 106. Based on a reception of the location information, the circuitry 202 may determine a distance of each of the plurality of medical facilities (such as medical facilities 804 and 806) from the geographic location 802 of the vehicle 104. Based on the determination, the distance of a medical facility with a shortest distance from the vehicle 104 among that of the plurality of medical facilities may be determined as the first distance. The circuitry 202 may control the actuator 404B to regulate an amount of the one or more medicaments that may need to be applied on at least one body part (such as parts 506, 604A, or 604B) of the occupant 112 based on the medical facility (such as medical facilities 804 or 806) at the first distance. For example, the first medical facility 804 may be at a distance of 10 miles from the location 802 of the vehicle 104 and the second medical facility 806 is at a distance of 15 miles from the location 802 of the vehicle 104. Therefore, the first medical facility 804 may be the determined medical facility and 10 miles may be considered as the first distance. The amount of one or more medicaments to be sprayed on at least one body part of the occupant 112 may be decided based on the first distance (i.e., 10 miles). In general, if the distance of the medical facility from the vehicle 104 is greater, then it is assumed that it will take longer for emergency services to reach the location of the vehicle 104. Therefore, the amount of medicament dispensed may be more for a distant medical facility as compared to that for a nearby medical facility. In an embodiment, the circuitry 202 may transmit information about the dispensed one or more medicaments and the at least one body part of the occupant 112 that required medical attention or a medical intervention to a server (such as the server 106) related to the medical facility.

In accordance with an embodiment, the circuitry 202 may be configured to receive medical history information of the occupant 112. Based on the received medical history information, the circuitry 202 may control the one or more medicament dispensers 118 to dispense one or more medicaments on at least one body part (such as parts 506, 604A, or 604B). The medical history information of the occupant may be stored on the server 106, the database associated with the server, the memory 204, or the memory 304. Based on the collision event 110, the circuitry 202 may be configured to receive the medical history information. For example, the medical history of the occupant 112 may include that the occupant 112 is type-2 diabetic. Based on the medical history, insulin may be dispensed (i.e., injected) inside the body of the occupant 112. In an embodiment, the circuitry 202 may transmit information about the dispensed one or more medicaments and the medical history information of the occupant 112 to a server (such as the server 106) related to the medical facility.

Figure 9:
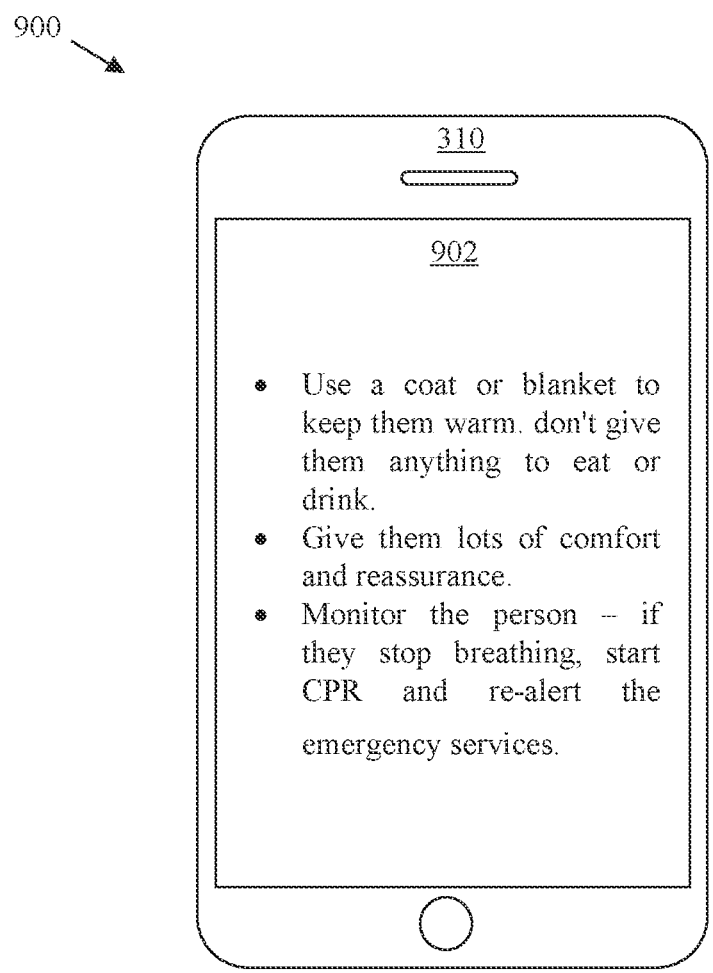
FIG. 9 is a diagram that illustrates an exemplary output device associated a vehicle for rendering first aid information, in accordance with an embodiment of the disclosure.

FIG. 9 is a diagram that illustrates an exemplary output device associated a vehicle for rendering first aid information, in accordance with an embodiment of the disclosure. FIG. 9 is explained in conjunction with elements from FIGS. 1, 2, 3, 4, 5, 6, 7, and 8. With reference to FIG. 9, there is shown an exemplary diagram 900 of an output device 310 associated the vehicle 104 for rendering first aid information.

During operation, the circuitry 202 may be configured to determine first aid information based on the set of health parameters. The first aid information may correspond to a medical assistance for the at least one body part (such as parts 506, 604A, or 604B) of the occupant 112. In an embodiment, the circuitry 202 may be configured to control the output device 310 associated with the vehicle 104 to render the determined first aid information on a graphical user interface (GUI) 902 of the output device 310. As illustrated, for example, the first aid information displayed on the GUI 902 may be "Use a coat or blanket to keep them warm. Don't give them anything to eat or drink", "Give them lots of comfort and reassurance", or "Monitor the person—if they stop breathing, start CPR and re-alert the emergency services".

In another embodiment, the output device 310 may be an audio generating device that can be used to render the determined first aid information in a particular audio format. For example, after the collision event 110, the blood pressure of the occupant 112 may be abnormal. Based on the abnormality, first aid information may be generated. The generated first aid information may be "Focus on your breathing. Take a few deep breaths and hold them for a few seconds before releasing". The generated first aid information may also be rendered on the output device 310.

Figure 10:
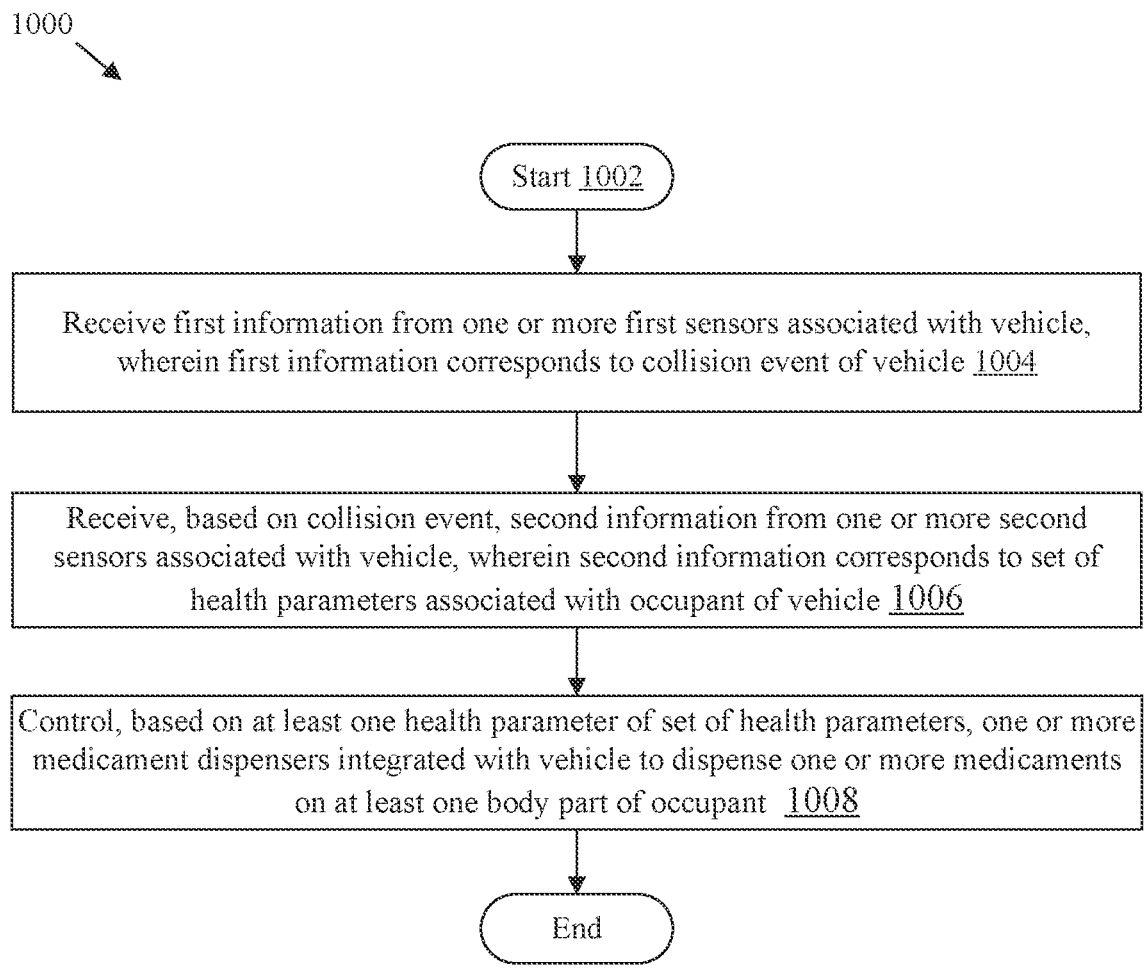
FIG. 10 is a flowchart that illustrates exemplary operations for control of a medicament dispenser based on a collision event, in accordance with an embodiment of the disclosure.

FIG. 10 is a flowchart that illustrates exemplary operations for control of medicament dispenser based on a collision event, in accordance with an embodiment of the disclosure. With reference to FIG. 10, there is shown a flowchart 1000. The flowchart 1000 is described in conjunction with FIGS. 1, 2, 3, 4, 5, 6, 7, 8, and 9. The operations from 1002 to 1008 may be implemented, for example, by the circuitry 202 of the electronic device 102 or the electronic control unit 302 of the vehicle 104. The operations of the flowchart 1000 may start at 1002 and proceed to 1004.

At 1004, first information may be received from the one or more first sensors 114 associated with the vehicle 104. The circuitry 202 may be configured to receive the first information from the one or more first sensors 114 associated with the vehicle 104. The first information may correspond to the collision event 110, the intensity of the collision event 110, or a direction of the collision event (such as the direction 408). Details about the collision event 110, the intensity of the collision event 110, and direction of the collision event (such as the direction 408) of the vehicle 104 are provided, for example, in FIGS. 4, 5, and 6.

At 1006, second information from the one or more second sensors 116 associated with the vehicle 104 may be received. The circuitry 202 may be configured to receive, based on the collision event 110, the second information from the one or more second sensors 116 associated with the vehicle 104. The second information may correspond to the set of health parameters associated with the occupant 112 of the vehicle 104. Details about the set of health parameters are provided, for example, in FIGS. 4, 5, and 6.

At 1008, the one or more medicament dispensers 118 may be controlled to dispense one or more medicaments on at least one body part (such as parts 506, 604A or 604B) of the occupant 112. The circuitry 202 may be configured to control, based on the at least one health parameter of the set of health parameters, the one or more medicament dispensers 118 integrated into the vehicle 104 to dispense one or more medicaments on at least one body part (such as parts 506, 604A, or 604B) of the occupant 112. Details about the one or more medicament dispensers 118 are provided, for example, in FIGS. 4, 5, 6, and 7.

Various embodiments of the disclosure may provide a non-transitory, computer-readable medium and/or storage medium, and/or a non-transitory machine readable medium and/or storage medium stored thereon, a set of instructions executable by a machine and/or a computer (such as the electronic device 102 or the vehicle 104). The set of instructions may be executable by the machine and/or the computer to perform operations that may include acquiring the first information from the one or more first sensors 114 associated with the vehicle 104. The first information may correspond to the collision event 110 of the vehicle 104. The operations may further include acquiring the second information from the one or more second sensors 116 associated with the vehicle 104 based on the collision event 110. The second information may correspond to the set of health parameters associated with the occupant 112 of the vehicle 104. The operations may further include controlling the one or more medicament dispensers 118 integrated into the vehicle 104 based on the at least one health parameter of the set of health parameters to dispense one or more medicaments on at least one body part (such as parts 506, 604A, or 604B) of the occupant 112.

The present disclosure may be realized in hardware, or a combination of hardware and software. The present disclosure may be realized in a centralized fashion, in at least one computer electronic device, or in a distributed fashion, where different elements may be spread across several interconnected computer electronic devices. A computer electronic device or other apparatus adapted for carrying out the methods described herein may be suited. A combination of hardware and software may be a general-purpose computer electronic device with a computer program that, when loaded and executed, may control the computer electronic device such that it carries out the methods described herein. The present disclosure may be realized in hardware that includes a portion of an integrated circuit that also performs other functions. It may be understood that, depending on the embodiment, some of the steps described above may be eliminated, while other additional steps may be added, and the sequence of steps may be changed.

The present disclosure may also be embedded in a computer program product, which includes all the features that enable the implementation of the methods described herein, and which when loaded in a computer electronic device is able to carry out these methods. Computer program, in the present context, means any expression, in any language, code or notation, of a set of instructions intended to cause an electronic device with an information processing capability to perform a particular function either directly, or after either or both of the following: a) conversion to another language, code or notation; b) reproduction in a different material form. While the present disclosure has been described with reference to certain embodiments, it will be understood by those skilled in the art that various changes may be made, and equivalents may be substituted without departing from the scope of the present disclosure. In addition, many modifications may be made to adapt a particular situation or material to the teachings of the present disclosure without departing from its scope. Therefore, it is intended that the present disclosure is not limited to the particular embodiment disclosed, but that the present disclosure will include all embodiments that fall within the scope of the appended claims.

What is claimed is:

1. An electronic device, comprising:
   circuitry configured to:
   receive first information from one or more first sensors associated with a vehicle, wherein the first information corresponds to a collision event of the vehicle;
   receive, based on the collision event, second information from one or more second sensors associated with the vehicle, wherein the second information corresponds to a set of health parameters associated with an occupant of the vehicle;
   determine, based on the second information corresponding to the set of health parameters associated with the occupant of the vehicle, an injury to at least one body part of the occupant of the vehicle and a severity of the injury to the at least one body part; and
   control, based on the severity of the injury to the at least one body part and at least one health parameter of the set of health parameters, one or more medicament dispensers integrated into at least one of a center console, a seat, an armrest, a door, a dashboard, or a ceiling of the vehicle to dispense one or more medicaments on the injury to the at least one body part of the occupant, wherein each of the one or more medicament dispensers comprises:
   a medicament reservoir integrated in the vehicle, wherein the medicament reservoir is configured to store a medicament of the one or more medicaments,
   a nozzle integrated in the vehicle and communicably coupled to the medicament reservoir, wherein the nozzle is configured to dispense the medicament and is positioned at a first location, wherein the first location is proximate to a second location of the occupant, and an actuator communicably coupled to the nozzle and the medicament reservoir, wherein the actuator is configured to release the medicament from the medicament reservoir.

2. The electronic device according to claim 1, wherein the circuitry is further configured to: control the actuator to release the medicament from the medicament reservoir on the at least one body part of the occupant, via the nozzle.

3. The electronic device according to claim 2, wherein the first information further corresponds to an intensity of the collision event, wherein the circuitry is further configured to: control, based on the intensity of the collision event, the actuator to regulate an amount of the medicament on the at least one body part of the occupant.

4. The electronic device according to claim 2, wherein the first information further corresponds to a direction of the collision event, wherein the circuitry is further configured to: control, based on the direction of the collision event, the actuator to regulate an amount of the medicament on the at least one body part of the occupant.

5. The electronic device according to claim 2, wherein the second information is received until a predefined time-period from a time of the collision event, wherein the circuitry is further configured to: control, after a completion of the predefined time-period, the actuator to regulate an amount of the medicament on the at least one body part of the occupant.

6. The electronic device according to claim 1, wherein the set of health parameters comprises a first set of health parameters that relates to a plurality of images of the occupant in the collision event, and wherein the circuitry is further configured to:

compare the plurality of images of the occupant in the collision event with a pre-stored plurality of images of the occupant, wherein the pre-stored plurality of images is captured by the one or more second sensors in an event of the vehicle, the event is different from the collision event;

determine, based on the comparison, the at least one body part of the occupant to dispense the one or more medicaments; and control the one or more medicament dispensers to regulate an amount of the one or more medicaments on the at least one body part of the occupant, based on the determination.

7. The electronic device according to claim 1, wherein the set of health parameters comprises a second set of health parameters that relates to a plurality of biological parameters of the occupant in the collision event, and wherein the circuitry is further configured to:

compare the plurality of biological parameters of the occupant in the collision event with pre-stored biological parameters of the occupant, wherein the pre-stored biological parameters are measured by the one or more second sensors in an event of the vehicle, the event is different from the collision event;

determine, based on the comparison, the at least one body part of the occupant to dispense the one or more medicaments; and control the one or more medicament dispensers to regulate an amount of the medicament on the at least one body part of the occupant, based on the determination.

8. The electronic device according to claim 7, wherein the plurality of biological parameters may relate to at least one of: a blood pressure, a heart rate, a pulse rate, a breath rate, a body weight, or a body temperature.

9. The electronic device according to claim 2, wherein the circuitry is further configured to:

receive third information that corresponds to a geographic location of the vehicle;

determine a medical facility at a first distance from the geographic location of the vehicle; and control the actuator to regulate an amount of the medicament on the at least one body part of the occupant, based on the determined medical facility at the first distance.

10. The electronic device according to claim 1, wherein the circuitry is further configured to control an output device associated with the vehicle to render first aid information based on the set of health parameters, and wherein the first aid information corresponds to a medical assistance for the at least one body part of the occupant.

11. The electronic device according to claim 1, wherein the one or more medicament dispensers are communicably coupled to a life support device integrated into the vehicle, the life support device is configured to be coupled to a body part of the occupant, and wherein the circuitry is further configured to:

control, based on the at least one health parameter of the set of health parameters, the life support device, to recover the body part of the occupant injured based on the collision event.

12. The electronic device according to claim 11, wherein the life support device comprises at least one of: a defibrillator, a cardiopulmonary resuscitation (CPR) device, or a breathing support device.

13. The electronic device according to claim 1, wherein the one or more first sensors comprises at least one of: an impact detection sensor, a crash impact sound sensor, an accelerometer sensor, or a pressure sensor; and wherein the one or more second sensors comprise at least one of: an image sensor, a position sensor, a blood pressure sensor, a heart rate sensor, a pulse rate sensor, a sound detection sensor, a weight sensor, or a temperature sensor.

14. The electronic device according to claim 1, wherein the circuitry is further configured to:

receive medical history information of the occupant; and control, based on the received medical history information, the one or more medicament dispensers to dispense the one or more medicaments on the at least one body part.

15. The electronic device according to claim 1, wherein the circuitry is further configured to transmit information about dispensed one or more medicaments and medical information of the occupant to a server related to a medical facility.

16. The electronic device according to claim 1, wherein the circuitry is further configured to:

receive third information that corresponds to a geographic location of the vehicle; and control the one or more medicament dispensers to regulate an amount of the one or more medicaments on the at least one body part of the occupant, based on the received third information.

17. A computer-implemented method, comprising:

receiving first information from one or more first sensors associated with a vehicle, wherein the first information corresponds to a collision event of the vehicle;

receiving, based on the collision event, second information from one or more second sensors associated with the vehicle, wherein the second information corresponds to a set of health parameters associated with an occupant of the vehicle;

determining, based on the second information corresponding to the set of health parameters associated with the occupant of the vehicle, an injury to at least one body part of the occupant of the vehicle and a severity of the injury to the at least one body part;

controlling, based on the severity of the injury to the at least one body part and at least one health parameter of the set of health parameters, one or more medicament dispensers integrated into at least one of a center console, a seat, an armrest, a door, a dashboard, or a ceiling of the vehicle to dispense one or more medicaments on the injury to the at least one body part of the occupant, wherein each of the one or more medicament dispensers comprises:

a medicament reservoir integrated in the vehicle, wherein the medicament reservoir is configured to store a medicament of the one or more medicaments, a nozzle integrated in the vehicle and communicably coupled to the medicament reservoir, wherein the nozzle is configured to dispense the medicament and is positioned at a first location, wherein the first location is proximate to a second location of the occupant, and an actuator communicably coupled to the nozzle and the medicament reservoir, wherein the actuator is configured to release the medicament from the medicament reservoir; and controlling the actuator to release the medicament from the medicament reservoir on the injury to the at least one body part of the occupant via the nozzle.

18. The method according to claim 17, wherein the first information further corresponds to an intensity of the collision event, further comprising:

controlling, based on the intensity of the collision event, the one or more medicament dispensers to regulate an amount of the one or more medicaments on the at least one body part of the occupant.

19. The method according to claim 17, wherein the set of health parameters comprises a first set of health parameters that relates to a plurality of images of the occupant in the collision event, further comprising:

comparing the plurality of images of the occupant in the collision event with a pre-stored plurality of images of the occupant, wherein the pre-stored plurality of images is captured by the one or more second sensors in an event of the vehicle, the event is different from the collision event;

determining, based on the comparison, the at least one body part of the occupant to dispense the one or more medicaments; and controlling the one or more medicament dispensers to regulate an amount of the one or more medicaments on the at least one body part of the occupant, based on the determination.

20. A vehicle, comprising:

one or more medicament dispensers integrated into at least one of a center console, a seat, an armrest, a door, a dashboard, or a ceiling of the vehicle; and circuitry communicably coupled to the one or more medicament dispensers, wherein the circuitry is configured to:

acquire first information from one or more first sensors associated with the vehicle, wherein the first information corresponds to a collision event of the vehicle;

acquire, based on the collision event, second information from one or more second sensors associated with the vehicle, wherein the second information corresponds to a set of health parameters associated with an occupant of the vehicle;

determine, based on the second information corresponding to the set of health parameters associated with the occupant of the vehicle, an injury to at least one body part of the occupant and a severity of the injury to the at least one body part;

control, based on the severity of the injury to the at least one body part and at least one health parameter of the set of health parameters, the one or more medicament dispensers to dispense one or more medicaments on the injury to the at least one body part of the occupant, wherein each of the one or more medicament dispensers comprises:

a medicament reservoir integrated in the vehicle, wherein the medicament reservoir is configured to store a medicament of the one or more medicaments, a nozzle integrated in the vehicle and communicably coupled to the medicament reservoir, wherein the nozzle is configured to dispense the medicament and is positioned at a first location, wherein the first location is proximate to a second location of the occupant, and an actuator communicably coupled to the nozzle and the medicament reservoir, wherein the actuator is configured to release the medicament from the medicament reservoir; and control the actuator to release the medicament from the medicament reservoir on the injury to the at least one body part of the occupant via the nozzle.

* * * * *